United States Patent [19]

Greene et al.

[11] Patent Number: 5,614,648

[45] Date of Patent: Mar. 25, 1997

[54] ANTIOXIDANT GLYCERIDE DERIVATIVES

[76] Inventors: George H. Greene, P.O. Box 2384, Morristown, N.J. 07962; Robert Miller, 740 Island Ct., Columbus, Ohio 43214; James L. Williams, 819 Crofton Cir., Reynoldsburg, Ohio 43068; James C. Phillips, 510 W. Main St., Plain City, Ohio 43064; Jerry F. Stults, 4270 Stover Rd., Ostrander, Ohio 43061; Jan P. E. Tellings, 3151 Parsons Ave., Columbus, Ohio 43207

[21] Appl. No.: 370,884

[22] Filed: Jan. 10, 1995

Related U.S. Application Data

[60] Division of Ser. No. 799,061, Nov. 27, 1991, Pat. No. 5,380,890, which is a continuation-in-part of Ser. No. 488,719, Feb. 28, 1990, Pat. No. 5,152,244.

[51] Int. Cl.$^6$ .................................................. C07C 51/50
[52] U.S. Cl. .......................... 554/4; 554/2; 554/5; 554/7; 252/397; 252/399; 252/400.2; 252/400.23; 252/401; 252/403; 252/404; 252/407; 560/2; 560/3; 560/4; 564/152; 564/155; 564/161; 564/182
[58] Field of Search ........................... 554/2, 5, 7, 4; 252/397, 399, 400.2, 400.23, 401, 403, 404, 407

[56] References Cited

U.S. PATENT DOCUMENTS

| | | | |
|---|---|---|---|
| 3,644,482 | 2/1972 | Dexter et al. | 584/7 |
| 4,058,502 | 11/1977 | Dexter et al. | 554/7 |
| 4,093,587 | 6/1978 | Spivack | 584/5 |

*Primary Examiner*—Deborah D. Carr
*Attorney, Agent, or Firm*—Burns, Doane, Swecker & Mathis, L.L.P.

[57] ABSTRACT

A method of producing an antioxidant containing derivatives of an organic compound, and in particular, an antioxidant glyceride derivative, comprises reacting a first compound with a second medium. By this reaction, a product is formed whereby an active component of the first compound, e.g., an antioxidant moiety, is covalently incorporated into the second medium.

The second medium comprises glyceride derivatives, silicones, fluorocarbons and alkoxylates containing reactive groups such as hydroxy, amino, carboxyl, ester, or amides.

7 Claims, No Drawings

ANTIOXIDANT GLYCERIDE DERIVATIVES

CROSS-REFERENCE TO RELATED APPLICATIONS

This application is a divisional of application Ser. No. 07/799,061 filed Nov. 27, 1991, which is now U.S. Pat. No. 5,380,890, which is continuation-in-part of application Ser. No. 07/488,719, filed Feb. 28, 1990, which is now U.S. Pat. No. 5,152,244, each of which are incorporated by reference in their entirety.

BACKGROUND OF THE INVENTION

The present invention relates to a method of solubilizing a compound in a medium such as a lubricating composition.

The use of antioxidants as stabilizing materials for lubricant compositions employed with synthetic fibers is known in the art as a means to increase the thermal stability of the lubricant.

However, as process speeds for manufacturing these synthetic fibers have increased, the need for even greater thermal stability of the lubricant has become evident. Improved thermal stability would be effective in reducing the excessive volatility which is present at high temperature points within, for example, the drawing and heat setting processes.

In addition, a lubricant composition having a very high thermal stability would remain fluid at these high temperature process points. Accordingly, if the lubricant is sufficiently stable, any lubricant accumulation occurring at these points will be removed by the continuous wiping action as the fibers are processed. As a result, maintenance costs could be reduced and fiber quality could also be improved because deleterious frictional changes could be effectively eliminated.

As was previously noted, antioxidants are commonly used to enhance the thermal stability of lubricants. However, the need for even greater thermal stability necessitates very high concentrations of antioxidants in lubricant formulations.

Moderate levels of antioxidant can be achieved with compositions such as butylated hydroxytoluene (BHT). Unfortunately, BHT and similar antioxidants have substantial volatility at temperatures used to manufacture and process synthetic fiber. Consequently, this class of antioxidants volatilize rapidly and fail to prevent oxidation.

Other known phenolic antioxidants such as Irganox 1010 which have low volatility also have limited solubility in lubricant formulations. As a result, the requisite high antioxidant concentration cannot be effectively attained.

Thus, the need still exists for a method of increasing the solubility of compounds such as antioxidants in medium in which the compound have only limited solubility, i.e., lubricant compositions.

Accordingly, it is an object of the present invention to provide a method for solubilizing compounds in a medium.

It is a further object to provide a thermally stable lubricant/surfactant composition containing antioxidant groups.

It is still a further object of the present invention to provide lubricant/surfactant compositions which have antioxidant moieties covalently bonded into their structures in order to avoid excessive volatility as well as problems associated with limited solubility.

SUMMARY OF THE INVENTION

In accordance with the foregoing objectives, the present invention relates to a method of solubilizing a first compound in a second medium where the first compound has a limited solubility in the second medium. In particular, the method comprises the reacting of the first compound with the second medium. By this reaction, a product is formed whereby an active component of the first compound is covalently incorporated into the second medium.

Preferably, the first compound comprises an antioxidant which contains a group capable of reacting with a reactive group in the second component.

Furthermore, the second medium preferably comprises at least one compound having the following formula:

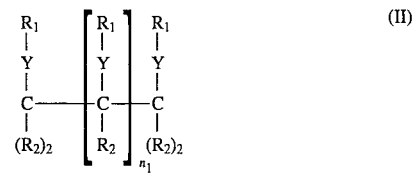
(II)

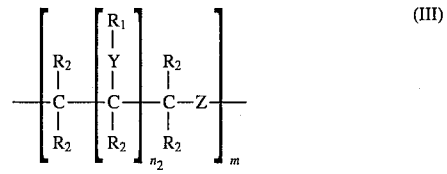
(III)

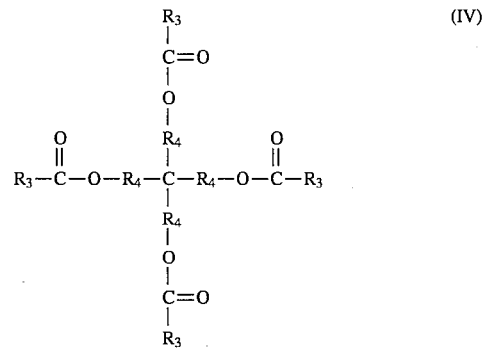
(IV)

wherein Y can be the same or different and comprises

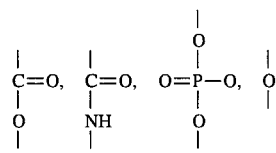

with the provisos that
(i) where Y is

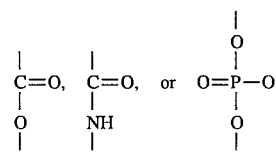

the corresponding $R_1$ group comprises
  a cyclic or acyclic, an unsubstituted or a hydroxy, carboxy, or halogen substituted alkyl, alkenyl, alkynl, or oxyalkylene group or a sulfur, nitrogen or phosphorus derivative of an alkyl, alkenyl, alkynl, or oxyalkylene group, an unsubstituted or substituted aryl group, or mixtures thereof,
and (ii) where Y is $$\begin{array}{c} | \\ O, \\ | \end{array}$$

the corresponding $R_1$ group can be hydrogen, in addition to the above described compounds, with the further proviso that if Y is $$\begin{array}{c} | \\ O, \\ | \end{array}$$

and $R_1$ is not hydrogen, at least one of the Y groups in the compound is not $$\begin{array}{c} | \\ O \\ | \end{array}$$

so that at least one of the Y-$R_1$ is reactive with the first compound;

and further wherein $R_2$ can be the same or different and comprises those $R_1$ groups described in proviso (ii) above, $R_3$ and $R_4$ can be the same or different and each comprise an alkyl group, Z can be an O, N, or P, $n_1=0-20$, $n_2=1-20$, and $m=1-100$.

DETAILED DESCRIPTION OF THE PREFERRED EMBODIMENTS

The present invention relates to a method for solubilizing a first compound in a second medium in which the first compound would otherwise have only a limited solubility. In particular, the method of the present invention relates to the reaction of the first compound with the second medium so as to covalently incorporate the first compound into the second medium.

The first compound and second medium each contain at least one reactive group which will react with a reactive group of the other. Accordingly, a moiety of the first compound will be covalently bonded to and thus effectively solubilized in the second medium by the reaction.

The first compound according to the present invention comprises at least one antioxidant which contains a reactive group capable of reacting with a reactive group in the second compound.

Preferably, the reactive group comprises —$CO_2R$, —OH, —$NR_2$, —CNR, or an oxyphosphorus residue wherein R is defined in the same manner as $R_2$ in the second compound.

In addition, the first compound preferably comprises di-tert-butyl-4-hydroxyhydrocinnamic (DTBH) acid and derivatives thereof, particularly esters, dialkyl or diaryl phosphonates, or trialkyl or triaryl phosphites, gallic acid and derivatives thereof, particularly ester derivatives such as propyl gallate, ascorbic acid and derivatives thereof, and citric acid and derivatives thereof, particularly ester derivatives.

Specific examples of suitable first compounds include hindered phenolic antioxidants such as the Irganox series (Irganox is a trademark of Ciba-Geigy).

The second medium comprises at least one glyceride derivative, silicone, fluorocarbon and alkoxylate containing reactive groups such as hydroxy, amino, carboxyl, ester, or amides. Examples of suitable second compound include aminosilicones such as Shin-Etsu KF-393, fluorocarbons such as perfluoroalcohol started alkoxylates, and glyceride derivatives having the following formula:

$$\begin{array}{c} R_1 \\ | \\ Y \\ | \\ C \\ | \\ (R_2)_2 \end{array} \left[ \begin{array}{c} R_1 \\ | \\ Y \\ | \\ C \\ | \\ R_2 \end{array} \right]_{n_1} \begin{array}{c} R_1 \\ | \\ Y \\ | \\ C \\ | \\ (R_2)_2 \end{array} \qquad (II)$$

$$\left[ \begin{array}{c} R_2 \\ | \\ C \\ | \\ R_2 \end{array} \right. \left[ \begin{array}{c} R_1 \\ | \\ Y \\ | \\ C \\ | \\ R_2 \end{array} \right]_{n_2} \left. \begin{array}{c} R_2 \\ | \\ C-Z \\ | \\ R_2 \end{array} \right]_m \qquad (III)$$

or $$\begin{array}{c} R_3 \\ | \\ C=O \\ | \\ O \\ | \\ R_3-C-O-R_4-C-R_4-O-C-R_3 \\ \phantom{R_3-C-O-R_4-}| \\ \phantom{R_3-C-O-R_4-}R_4 \\ \phantom{R_3-C-O-R_4-}| \\ \phantom{R_3-C-O-R_4-}O \\ \phantom{R_3-C-O-R_4-}| \\ \phantom{R_3-C-O-R_4-}C=O \\ \phantom{R_3-C-O-R_4-}| \\ \phantom{R_3-C-O-R_4-}R_3 \end{array} \qquad (IV)$$

wherein Y can be the same or different and comprises $$\begin{array}{cccc} | & | & | \\ C=O, & C=O, & O=P-O, & \text{or} & O \\ | & | & | & | \\ O & NH & O \\ | & | & | \end{array}$$

with the provisos that (i) where Y is $$\begin{array}{ccc} & & | \\ & & O \\ | & | & | \\ C=O, & C=O, & \text{or} \quad O=P-O \\ | & | & | \\ O & NH & O \\ | & | & | \end{array}$$

the corresponding $R_1$ group is cyclic or acyclic and comprises an unsubstituted or hydroxy, carboxy, or halogen substituted alkyl, alkenyl, alkynl, or oxyalkylene group; a sulfur, nitrogen or phosphorus derivative of the above alkyl, alkenyl, alkynl, or oxyalkylene groups; an unsubstituted or substituted aryl group; or mixtures thereof, and, (ii) where Y is $$\begin{array}{c} | \\ O, \\ | \end{array}$$

the corresponding $R_1$ group can be hydrogen, in addition to the above described compounds,
with the further proviso that if all of the Y groups are $$\begin{array}{c} | \\ O, \\ | \end{array}$$

then at least one of the corresponding $R_1$ groups is hydrogen so that at least one of the combinations of Y-$R_1$ is reactive with the first compound.

In addition, $R_2$ can be the same or different and comprises those $R_1$ groups described in proviso (ii) above,
$R_3$ comprises an alkyl group,
$R_4$ comprises an alkyl group,
Z can be an O, N, or P,
n1=0–20,
$n_2$=1–20, and
m=1–100.

Specific examples of classes of compounds according to formula II include glycerides, amides, and phospholipids while classes of compounds according to formula III include polyglycerols.

The reaction conditions selected for the reaction between the first compound and the second medium are dependent upon the reactants chosen and the desired composition of the final product. For example, the greater the ratio between the first compound and the second medium, the more —$R_1$ or —$R_3$ groups which will be substituted with the antioxidant group.

Moreover, this reaction according to the present invention may optionally occur in the presence of a catalyst in order to facilitate the reaction between the first compound and second medium.

In this regard, the correlation between reactants, catalysts, reaction conditions and the final products would be easily determined by those skilled in the art and thus are not further discussed herein.

The present invention also relates to the reaction product formed by the reaction of the first compound and the second medium.

In this product, a moiety of the first compound is covalently bonded to the second medium, thus allowing the first compound to be effectively solubilized into the second medium to a degree which otherwise would not be obtainable.

With respect to the preferred formulas above, this product is illustrated by formulas V, VI and VII below:

$$\begin{array}{c} Q \\ | \\ Y \\ | \\ C \\ | \\ (R_2)_2 \end{array} \left[ \begin{array}{c} Q \\ | \\ Y \\ | \\ C \\ | \\ R_2 \end{array} \right]_{n_1} \begin{array}{c} Q \\ | \\ Y \\ | \\ C \\ | \\ (R_2)_2 \end{array} \quad (V)$$

$$\left[ \begin{array}{ccc} & Q & \\ & | & \\ R_2 & Y & R_2 \\ | & | & | \\ -C- & -C- & -C-Z- \\ | & | & | \\ R_2 & R_2 & R_2 \end{array} \right]_m \quad (VI)$$

$$\begin{array}{c} Q \\ | \\ C=O \\ | \\ O \\ | \\ Q-C-O-R_4-C-R_4-O-C-Q \\ \| \quad\quad\quad | \quad\quad\quad \| \\ O \quad\quad R_4 \quad\quad O \\ | \\ O \\ | \\ C=O \\ | \\ Q \end{array} \quad (VII)$$

In these formula Y, Z, $R_1$, $R_2$, $_3$, $R_4$, $n_1$, $n_2$, and m are the same as defined above, and in formula (V) and (VI), Q comprises the first compound or —$R_1$ while in formula (VII), Q comprises the active component of the first compound or —$R_3$, with the further proviso that in each formula, at least one Q group comprises the first compound, i.e., an antioxidant moiety.

Preferably, the first compound comprises DTBH acid, a dialkyl or diaryl phosphinate, or a trialkyl or triaryl phosphite. Y preferably comprises $$\begin{array}{c} C=O, \\ O \end{array}$$

and $R_2$ comprises hydrogen.

Moreover, $R_1$ preferably comprises coconut oil residue having a chain length of $C_6$–$C_{18}$ which is unsaturated to yield an I.V. of 7–12.

In a preferred embodiment of the present invention, the solubility of an antioxidant in a medium in which it has limited solubility, i.e. a lubricant, can be increased.

It is important to recognize that while the following discussion focuses upon the preferred embodiment of the invention, one of ordinary skill in the art would clearly recognize that this discussion is equally applicable to other embodiments of the invention.

In this embodiment, an antioxidant is employed as the first compound while glyceride derivatives corresponding to formula II to VI are preferably employed as the second medium.

The preferred antioxidants are those where the reactive group of the first compound is —COOR (i.e., an ester) or an oxyphosphorus residue.

When the reactive group is —COOR, the first compound comprises:

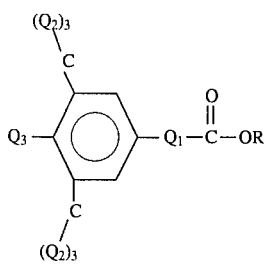  (VIII)

where $Q_1$ is an alkyl or an oxyalkylene group, $Q_2$ is H, or an alkyl group and $Q_3$ is —OH or —SH and the R group is an alkyl, aryl or alkyloxy group.

When the reactive group is defined as an oxyphosphorus group, the first compound includes those phosphate, phosphite, phosphonate, and phosphinite compounds which are respectively illustrated below.

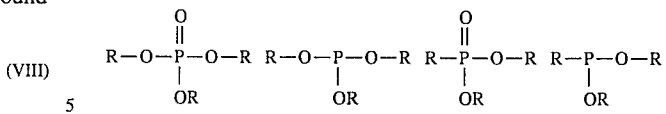

In each case the R group may be the same or different and comprises, aryl groups, alkyl groups, alkyloxy groups, oxyalkylene groups, or mixture thereof, which may be unsubstituted or substituted with hydroxy or groups containing sulfur or phosphorus atoms.

Examples of antioxidants which are employed with the present invention include sterically hindered phenols, as well as phosphinates, phosphites and sulfides. Specific compounds which can be employed include IRGANOX 1010, IRGANOX 1076, IRGANOX 259, IRGANOX 1098, IRGANOX 245 (IRGANOX is the trademark of Ciba-Geigy). Examples of these compounds are illustrated below.

Irganox 1010

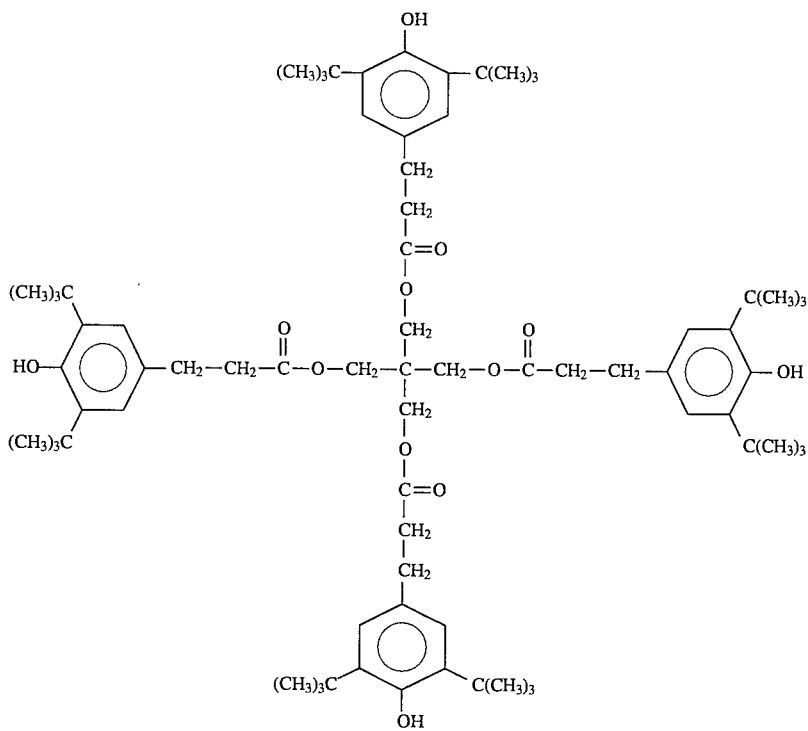

Irganox 1076

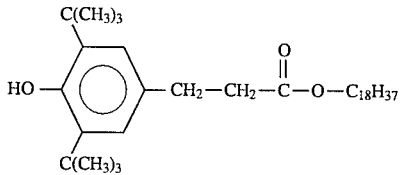

Irganox 1098

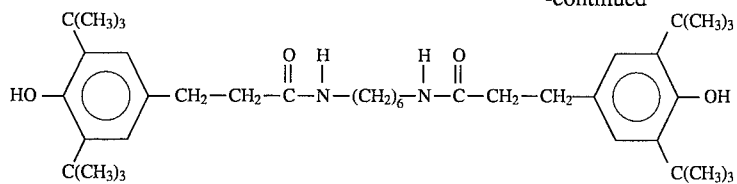
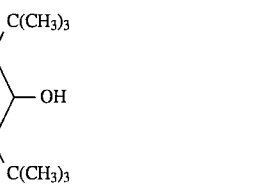

Irganox 245

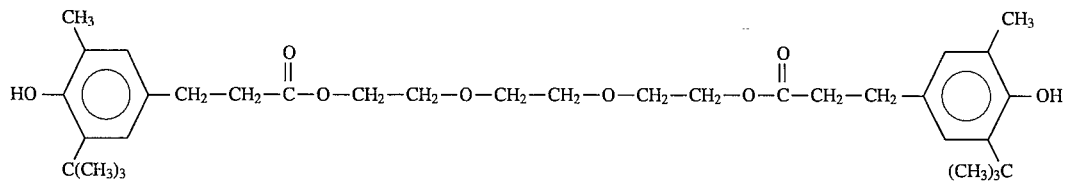

Irganox 259

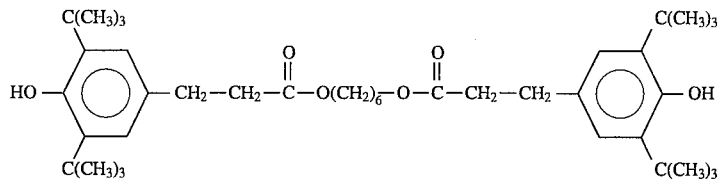

The glycerides which can be effectively employed as the second medium in the present invention include those glycerides and polyglycerols, polyols, and esters (both mono- and polyfunctional) which contain organic acids groups with carbon groups having carbon chain lengths of $C_1$–$C_{50}$. In addition, these compositions may contain other groups such as polyoxyalkylene groups which are bonded to the carbon skeletal (e.g., glyceride) structure.

Specific examples of these compositions include those based on natural oils and their hydrogenated and/or alkoxylated analogs, for example, palm kernel oil, canola oil, coconut oil, soybean oil, sunflower oil and high-oleic sunflower oil, castor oil, mink oil, shea oil, castor wax, other glycerides such as glycerol tripelargonate, glycerol trioleate, glycerol tricaproate, and other polyglycerol or polyol esters, alkoxylated coconut oil, alkoxylated castor oil, triglycerol dioleate, hexaglycerol dioleate, decaglycerol dioleate, trimethylol propane (or TMP)-tripelargonate, trimethylol ethane (or TME)-tripelargonate, TMP-tri-isostearate, TME-tri-isostearate, sorbitan oleates, stearates, and isostearates, pentaerythritol tetra-pelargonate and propylene glycol di-ethylhexanoate, with coconut oil, hydrogenated coconut oil, alkoxylated castor oil, and hydrogenated, alkoxylated castor oil being the more preferred compounds.

In this embodiment, a composition according to the present invention is provided by the reaction between the first compound and the second medium. This reaction is generally classified as either an interesterification, or transesterification reaction of a glyceride with an antioxidant, or a direct esterification reaction.

In either case, the antioxidant is preferably present in the reaction mixture in an amount which is effective in providing a "superstable lubricant" when the reaction is performed. This amount is greater than zero but preferably less than 30% by weight of the reaction mixture.

By the term "superstable lubricant" it is meant that the antioxidant contained therein does not salt out.

The stability of the lubricant can be illustrated by the time needed for the lubricant to polymerize, i.e., to change from a free-flowing liquid into a gel or a solid. The larger the value for the time to polymerization, the more stable the lubricant.

A "superstable lubricant" according to the present invention has a value of greater than about 150 minutes when upwards of 10% of the antioxidant is covalently bound into the lubricant.

It should be noted that such values are much greater than the less than 30 minute value associated with traditional lubricant compositions.

These values are based on "oven stability tests" of the lubricant. In this test, approximately 200 mg samples of lubricant is weighed into aluminum weigh pans and placing said pans in an oven (manufactured by Gruenberg) held at 250 degrees Centigrade (+/−10 degrees) until the lubricant sample has polymerized, i.e., the sample is no longer fluid.

In addition to the glyceride and antioxidant reactants, this embodiment preferably utilizes a catalytic material in order to promote the reaction.

The catalysts which are effective within this embodiment of the present invention are those known in the art and include sodium methylate, potassium hydroxide, and sodium hydroxide, and sodium/potassium metal alloy with sodium methylate being most preferred.

This catalyst is preferably present in an amount of about 0.02 to about 2% by weight of the reactant materials with approximately 1% by weight being most preferred.

The glycerides (or other esters) are preferably present in an amount greater than about 40% by weight of the reaction mixture, with about 90% by weight of the reaction mixture being more preferred.

The rearrangement or transesterification reaction can be performed by any known method within the art such as those described within Bailey's Industrial Oil and Fat Products.

For example, a batch process can be employed where the triglyceride and the antioxidant are mixed together in a vacuum and heated to a temperature of about 90° C. to about 105° C. Then, while still under vacuum, the catalytic material is added and mixed into the reaction mixture. The vacuum can be removed as mixing is continued. The product is then heated, filtered, bleached and deodorized.

The resulting product is an antioxidant glyceride derivative which contains up to about 20% by weight of an antioxidant. As can be plainly seen, this solubility is much greater than the about 1% solubility which can be obtained by traditional methods.

In another method according to the invention, the above described antioxidant glyceride derivatives can be made through a direct esterification reaction.

In this aspect of the invention, the polyglycerols (i.e., second medium) are reacted with the first compound which comprises certain acids such as pelargonic acid, coconut fatty acids, and the like as well as hindered-phenolic acids such as DTBH (di-tert butyl hydroxyhydrocinnamic acid). Such direct esterification processes are also well known in the art and are not further described herein.

These compounds can be used as a lubricant for either natural, e.g., proteinaceous or natural cellulostic fibers, or synthetic fibers, e.g., polyesters, nylons, polypropylene, acrylic, aramid, or synthetic cellulostic fibers.

These compounds according to the present invention can be applied to a fiber in any conventional method known in the art, such as those described within U.S. Pat. No. 3,853,607; U.S. Pat. No. 4,390,591; and Proffitt and Patterson (JAOCS, Vol. 65, No. 10, 1988) which are incorporate herein by reference.

As a consequence of their exceptional thermal stability, these preferred antioxidant derivatives may also find utility as lubricants for internal combustion engines, gear boxes, transmissions and the like. For these uses, they may be formulated with selected oils, glycerides and various esters, detergents, and extreme pressure additives which are recognized in the art.

These compositions are particularly desirable with two-stroke engines because of their biodegradability. As a result, two-stroke engines lubricated with the subject compositions are environmentally sensitive when used in waterways, lakes, and impoundments when used to propel water craft. Similarly, use of these compositions as chain saw lubricants are expected to have less effect on the environment if a spill or leakage occurs.

Because of the combination of high temperature stability and biodegradability, these compositions can be employed as hydraulic fluids and power transmission fluids for earth moving equipment and the like. Similarly, these compositions can be employed as cutting lubricants used in the machining of metal parts. For such an application, the subject compositions may be formulated with surfactants to facilitate emulsification.

Because of very high temperature requirements, the compositions of the present invention can be employed as solder assist fluids. Solder assist fluids are used in the fabrication of circuit boards and require very high temperature stability because of prolonged exposure to molten solder. In such an application, the composition would contain antioxidant and sufficient polyoxyalkylene to make the subject composition either water dispersible or water soluble. This would allow cleansing of circuit boards with water instead of solvents which must be carefully recovered to avoid environmental contamination.

Additionally, these compositions according to the present invention can be employed as heat exchange fluids for high temperature applications.

In order to further illustrate the present invention, and the advantages thereof, the following specific examples are given. It being understood that same are intended solely as illustrative and in no way limitive.

EXAMPLES

EXAMPLE 1- PREPARATION BY TRANS- OR INTERESTERIFICATION

The following procedure illustrates the interesterification of Irganox 1010 with triglycerides or other esters. The Irganox 1010 and the oil was charged into a three necked round bottom flask with a nitrogen inlet, outlet, thermometer and agitator. The charge was heated to 110°–120° C. under nitrogen to remove water (typically for 20 minutes). The charge was cooled to approximately 90° C. Sodium methoxide was then added slowly. The amount is usually approximately 0.2% for low acid value oils. More sodium methoxide was required for high acid value oils. When sufficient sodium methoxide was added to the reaction, the charge turned red-brown in color and the smell of methyl esters was noted. If the charge did not turn red-brown, then there was not enough sodium methoxide in the batch. The reaction was held at 90°–110° C. for approximately one hour. Concentrated phosphoric acid (85%) was then added dropwise until the color became lighter. The amount of acid was usually around three quarters of the weight of sodium methoxide added. The batch was then water washed 3–4 times until the wash water remained at a pH of 5–6. The batch was then bleached and deodorized.

Example A

| | |
|---|---|
| 900.0 g | High oleic sunflower oil |
| 100.0 g | Irganox 1010 |
| enough sodium methoxide was added to change color and enough phosphoric acid was added to reverse color. | |

Example B

| | | |
|---|---|---|
| | 1400.0 g | pentaerythritol tetrapelargonate |
| | 155.6 g | Irganox 1010 |
| | 3.9 g | sodium methoxide |
| later | 3.5 g | 85% phosphoric acid |

Example C

| | | |
|---|---|---|
| | 1600.0 g | glycerol tri-pelargonate |
| | 177.8 g | Irganox 1010 |
| | 4.4 g | sodium methoxide |
| later | 3.9 g | 85% phosphoric acid |

Example D

| | |
|---|---|
| 270.0 g | RBF 76° coconut oil |
| 30.0 g | Irganox 1010 |
| enough sodium methoxide was added to change color and enough phosphoric acid to reverse color. | |

EXAMPLE 2- PREPARATION BY DIRECT ESTERIFICATION

A procedure for making esters from 3,5-di-tert-butyl-4-hydroxyhydrocinnamic acid (DTBH acid), fatty acids and polyol is as follows. The DTBH acid, appropriate fatty acids and desired alcohol is charged into a three necked round bottom flask. The flask is fitted with an agitator, thermometer, nitrogen inlet, and a reflux condenser topped with a condenser and a receiver. The charge is heated under a continuous flow of nitrogen until water begins to collect in the receiver (typically around 180° C.). The reaction is held at 180°–200° C. for 3–4 hours, then the temperature is raised to 235°–255° C. and held until the acid value is below 2.0 (usually 4–5 hours). The product is then cooled, bleached and deodorized.

Example E

| | |
|---|---|
| 278.4 g | DTBH acid (1.0 mole) |
| 2505.6 g | pelargonic acid (15.9 moles) |
| 573.6 g | pentaerythritol (4.2 moles) | on GLC-FAC assay, this composition would show approximately 10% DTBH acid and 90% pelargonic acid.

Example F

| | |
|---|---|
| 278.4 g | DTBH acid (1.0 mole) |
| 2505.6 g | Oleic acid (8.9 moles) |
| 303.8 g | 99.9% glycerol (3.3 moles) | on GLC-FAC assay, this composition would show approximately 10% DTBH acid and 90% oleic acid.

Example G

| | |
|---|---|
| 62.7 g | DTBH (0.23 moles) |
| 564.0 g | Oleic acid (2 moles) |
| 462 g | hexaglycerol (1 mole) | on GLC-FAC assay, this composition would show about 10% DTBH and 90% Oleic acid.

EXAMPLE 3- DIRECT ESTERIFICATION

A three necked 250 ml round bottom flask equipped with a motor driven mechanical stirrer and distillation setup is charged with 90 g of Shin-Etsu KF-393 (a tradename for an aminosilicone) and 10 g of 3,5-di-ter-butyl-4-hydroxyhydrocinnamic acid. the reaction mixture is heated at 160° C. for 6 hours. Progress of the reaction is monitored by infrared spectroscopy.

EXAMPLE 4- INTERESTERIFICATION

A three-necked round bottom flask (250 ml) equipped with a mechanical stirrer is charged with 90 g of Shin-Etsu KF-393 (a tradename for an aminosilicone) and 10 g of Irganox 1010. The mixture is heated at 160° C. for 6 hours under a blanket of nitrogen. The progress of the reaction is monitored by infrared analysis.

EXAMPLE 5- DIRECT ESTERIFICATION

A three necked 250 ml round bottom flask equipped with a motor driven stirrer and distillation setup is charged with 90 g of perfluoroalcohol started ethyleneoxide polymer and 10 g of DTBH acid. The reaction mixture is heated at 150° C. for 8 hours under a blanket of nitrogen. The progress of the reaction is monitored by the distillation of water and infrared spectroscopy.

EXAMPLE 6- INTERESTERIFICATION

A three neck round bottom flask (250 ml) equipped with a mechanical stirrer is charged with 90 g of a perfluoroalcohol started ethylene oxide polymer and 10 g of Irganox 1010. The mixture is blanketed with nitrogen and 1 g of sodium methoxide is added as a catalyst. The reaction mixture is heated to 150° C. and the temperature is maintained for 1 hour. The mixture is neutralized with phosphoric acid and the volatiles removed under reduced pressure.

EXAMPLE 7 - ESTERIFICATION

| STARTING MATERIAL | WEIGHT PERCENT | SUPPLIER |
|---|---|---|
| ETHOX HCO-16 | 89.39 | ETHOX CHEMICAL CO. |
| IRGANOX 1010 | 9.93 | CIBA-GEIGY |
| SODIUM METHOXIDE | 0.40 | |
| 85% PHOSPHORIC ACID | 0.28 | |
| 30% HYDROGEN PEROXIDE | 0.78* | |

*weight percent based on the weight of the product to be bleached

A reaction vessel, equipped with a heat source, stirring mechanism, nitrogen gas inlet, and a vacuum source was charged with Ethox HCO-16 (900 g, 89.39 wt %) and Irganox 1010 (100 g, 9.93 wt %). The contents are heated and stirred under a nitrogen atmosphere to a temperature of 120° C. (248° F). Once the Irganox 1010 has fully dissolved in the castor ethoxylate (typically 85°–95° C.), a vacuum was pulled on the reaction vessel to remove any water (typically 20 minutes at 1 mmHg). After the mixture was thoroughly dried, the vacuum was removed and the nitrogen atmosphere resumed.

At a temperature of 105°–120° C. (221°–248° F.), sodium methoxide (4.0 g, 0.50 wt %) was slowly added to the stirring mixture. Catalyst addition causes the reaction mixture to darken, and after approximately 20 minutes the color was nearly black, however, thin films of the reaction contents have a green tint. Once catalysis was confirmed by color change, the reaction was allowed to proceed for 120 minutes.

After the allotted reaction time, the mixture was allowed to cool to 90° C. (194° F.) and then quenched with 85% phosphoric acid (2.8 g, 0.28 wt %). The acid quench continued for a minimum of 30 minutes, and the temperature was maintained between 80°–90° C. (176°∝194° F.)The addition of acid caused the color of the reaction product to lighten significantly. Generally, the color was brownish-orange to orange. The product was filtered to remove and solid material. The temperature may be between 80°–90° C. (176°–194° F.) to facilitate the filtering process.

Once the filtering was complete, the reaction product was charged to a reaction vessel equipped with a heat source and stirring. The produce was stirred and heated to a temperature of 85°–90° C. (185°–194° F.). After the temperature has equilibrated, a 30% hydrogen peroxide solution (0.75 wt % based on charge of product) was slowly added to the stirring product. After the peroxide addition was complete, the stirring and heating are continued for 120 minutes. The yield of the rearranged product was 90–95%.

Finally, the bleached product was thoroughly mixed with an equivalent weight of the Ethox HCO-16 (i.e., 50/50 blend of product and starting material). The overall process resulted in approximately 1900 g of finished product. The final product was a 5 wt % loading of Irganox 1010 in a 16-mole hydrogenated castor oil ethoxylate. The color of the final product has ranged from dark orange to yellow, and the acid value was typically 2–3.

EXAMPLE 8 - COMPARATIVE RESULTS

The following comparative Tables illustrate the improvement in performance achieved with the present invention.

PERFORMANCE OF HIGH TEMPERATURE LUBRICANTS WITH OVEN TEMPERATURE MAINTAINED AT 250° C. (METHOD B)

| Acetone Composition Residue | Polymerization Time (minutes) | % Residue | % |
|---|---|---|---|
| coconut oil* | <30 | 17.6 | 17.7 |
| pentaerythritol 4-pelargonate* | <30 | 21.0 | 20.4 |
| glycerol tri-pelargonate* | <30 | 6.5 | 6.5 |
| coconut oil/ Irganox 1010 (1) | 210 | 24.1 | 19.6 |
| pentaerythritol 4-pelargonate/ Irganox 1010 (1) | 296 | 28.3 | 0.6 |
| glycerol tri-pelargonate/ Irganox 1010 (1) | 151 | 2.1 | 0.0 |
| coconut oil/ Irganox 1076 (1) | 153 | 26.5 | 25.0 |
| coconut oil/ Irganox 1076 (2) | 253 | 21.5 | 18.8 |
| Dimethyl-silicone (3)* | 254 | 97 | 97 |

*comparative example
(1) composition contains ten weight percent antioxidant
(2) composition contains twenty weight percent antioxidant
(3) UC Brand L-45; 50 cst The % Residue is the material remaining after thermal treatment in a Gruenberg oven.

Acetone is used to simulate process clean-up. Acetone % Residue is the material remaining after a triple acetone rinse/drying.

In both cases low residue is desirable. The use of the Irganox raises % Residue somewhat but not to an undesirable level. In all but one example, the presence of Irganox lowers Acetone % Residue. This is extremely desirable because easily removable residue facilitates clean-up of heater plates and other parts of the machinery used to manufacture fiber. Improvement in Acetone % Residue suggests that Irganox has impeded oxidatively induced crosslinking.

Clearly, the presence of Irganox effects a very major improvement in thermal stability as evidenced by much longer polymerization times. The control values are listed as less than thirty minutes because of the difficulty in determining lower values.

This test utilizes a standard laboratory oven made by Groen. Determination of the end point requires that the oven's door must be opened to see if the experimental sample has gelled. Because the oven temperature must stabilize, low polymerization times at this temperature can be inaccurate.

Pentaerythritol tetra-pelargonate is considered to be an industry standard for high temperature lubricant applications. Accordingly, the fact that coconut oil/Irganox derivative is at least seven times more stable; while the pentaerythritol/Irganox derivative is at least ten times more stable illustrates the advantages which can be associated with the present invention.

While the present invention has been described in terms of various preferred embodiments, the skilled artisan will appreciate that various modifications, substitutes, omissions, and changes may be made without departing from the spirit thereof. Accordingly it is intended that the scope of the present invention be limited solely by the scope of the following claims including equivalents thereof.

What is claimed is:

1. An antioxidant-containing derivative of an organic compound which comprises the following formula:

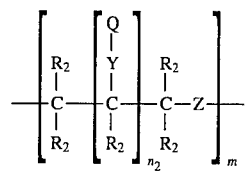

wherein Q, which can be the same or different, is an antioxidant moiety or $-R_1$ with the proviso that at least one Q is an antioxidant;

Y can be the same or different and is

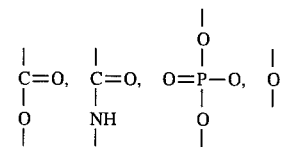

with the provisos that
(i) where Y is

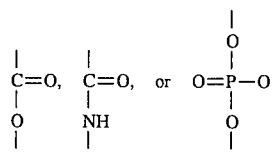

the corresponding $R_1$ groups, which can be the same or different, is a cyclic or acyclic, an unsubstituted or a hydroxy, carboxy, or halogen substituted alkyl, alkenyl, alkynl, or oxyalkylene group or a sulfur, nitrogen or phosphorus derivative of an alkyl, alkenyl, alkynl, or oxyalkylene group, an unsubstituted or substituted aryl group, or mixtures thereof, and (ii) where Y is

the corresponding $R_1$ group can be hydrogen, in addition to the above described compounds;

$R_2$ can be the same or different and comprises those $R_1$ groups described in proviso (ii) above, Z can be an O, N, or P, $n_2=1-20$, and $m=1-100$, with the proviso that $n_2$ and m cannot simultaneously be equal to 1.

2. The compound according to claim 1 where Y is

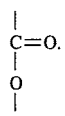

3. The compound according to claim 1 wherein Z is

4. The compound according to claim 1 where at least one $R_2$ is a hydrogen.

5. The compound according to claim 1 where at least one $R_1$ is a coconut oil residue having a chain length of $C_6$–$C_{18}$.

6. The derivative according to claim 1 wherein the antioxidant is present in an amount which is effective to provide a super stable lubricant.

7. An antioxidant-containing derivative of an organic compound which has the following formula:

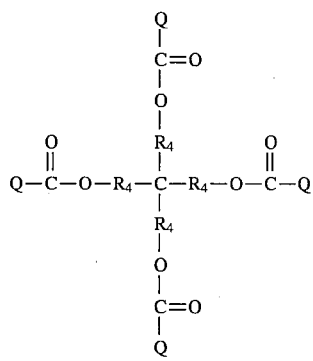

wherein Q is an antioxidant moiety or —$R_3$ with the proviso that (i) at least one Q is an antioxidant moiety and (ii) the antioxidant moieties are present in an amount up to about 20% by weight of the formula;

$R_3$ and $R_4$ can be the same or different and each comprise an alkyl group.

* * * * *